(12) United States Patent
Zhang et al.

(10) Patent No.: US 9,539,190 B2
(45) Date of Patent: Jan. 10, 2017

(54) SKIN CONDITIONING COMPOSITIONS CONTAINING 12-HYDROXYSTEARIC ACID

(75) Inventors: Qiqing Zhang, Shanghai (CN); Ezat Khoshdel, Wirral (GB); Teanoosh Moaddel, Trumbull, CT (US); Brian John Dobkowski, Trumbull, CT (US); Su Yuan, Shanghai (CN)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 13/695,440

(22) PCT Filed: May 5, 2011

(86) PCT No.: PCT/CN2011/000787
§ 371 (c)(1),
(2), (4) Date: Dec. 14, 2012

(87) PCT Pub. No.: WO2011/137664
PCT Pub. Date: Nov. 10, 2011

(65) Prior Publication Data
US 2013/0108566 A1    May 2, 2013

(30) Foreign Application Priority Data
May 7, 2010  (WO) ............... PCT/CN2010/000639

(51) Int. Cl.
| A61K 8/365 | (2006.01) |
| A61K 8/58 | (2006.01) |
| A61K 8/06 | (2006.01) |
| A61K 8/25 | (2006.01) |
| A61K 8/891 | (2006.01) |
| A61K 8/898 | (2006.01) |
| A61Q 19/00 | (2006.01) |

(52) U.S. Cl.
CPC ............... *A61K 8/365* (2013.01); *A61K 8/06* (2013.01); *A61K 8/25* (2013.01); *A61K 8/585* (2013.01); *A61K 8/891* (2013.01); *A61K 8/898* (2013.01); *A61Q 19/00* (2013.01); *A61K 2800/412* (2013.01); *A61K 2800/594* (2013.01)

(58) Field of Classification Search
None
See application file for complete search history.

(56) References Cited

U.S. PATENT DOCUMENTS

| 4,185,087 A | 1/1980 | Morlino |
| 4,467,125 A | 8/1984 | Chupp |
| 4,960,588 A | 10/1990 | Hoshowski |
| 5,106,109 A | 4/1992 | Tattersall et al. |
| 5,106,609 A | 4/1992 | Bolich, Jr. |
| 5,162,378 A | 11/1992 | Guthauser |
| 5,558,071 A | 9/1996 | Ward et al. |
| 5,759,524 A | 6/1998 | Tanner et al. |
| 5,833,967 A | 11/1998 | Ramin |
| 5,910,467 A | 6/1999 | Bragg |
| 5,955,003 A | 9/1999 | Terren |
| 6,197,343 B1 | 3/2001 | Minami et al. |
| 6,200,964 B1 | 3/2001 | Singleton |
| 6,228,377 B1 | 5/2001 | Sebillotte-Arnaud |
| 6,268,454 B1 | 7/2001 | Song |
| 6,269,817 B1 | 8/2001 | Nagashima |
| 6,350,441 B1 * | 2/2002 | Giles et al. ............... 424/70.12 |
| 6,379,680 B2 | 4/2002 | Gers-Barlag et al. |
| 6,423,325 B1 | 7/2002 | Alaluf et al. |
| 6,503,677 B1 | 1/2003 | Gutman et al. |
| 6,555,099 B2 | 4/2003 | Guskey |
| 6,579,851 B2 | 6/2003 | Goeke et al. |
| 6,592,856 B2 | 7/2003 | Giles |
| 6,680,285 B2 | 1/2004 | Abbas et al. |
| 6,710,092 B2 | 3/2004 | Scher et al. |
| 6,713,051 B2 | 3/2004 | Mayes et al. |
| 6,767,547 B2 | 7/2004 | Gers-Barlag et al. |
| 6,821,942 B2 | 11/2004 | Sebillotte-Arnaud et al. |
| 6,838,088 B2 | 1/2005 | Gers-Barlag et al. |
| 6,936,264 B2 | 8/2005 | Glenn, Jr. |
| 7,204,977 B2 | 4/2007 | Asai et al. |
| 7,282,236 B2 | 10/2007 | Michael |
| 8,021,651 B2 | 9/2011 | Hentrich |
| 8,461,129 B2 | 6/2013 | Bolduc et al. |
| 8,574,316 B2 | 11/2013 | Aimi |
| 8,747,828 B2 | 6/2014 | Dop |
| 2002/0054890 A1 | 5/2002 | Gers-Barlag |
| 2002/0071819 A1 * | 6/2002 | Giles et al. ............... 424/70.21 |
| 2002/0136743 A1 | 9/2002 | Langlois |
| 2003/0170188 A1 | 9/2003 | Ferrari |
| 2004/0043044 A1 | 3/2004 | Granger et al. |
| 2004/0044078 A1 | 3/2004 | Kawa |

(Continued)

FOREIGN PATENT DOCUMENTS

| CN | 1337224 | 2/2002 |
| CN | 1668270 A | 9/2005 |

(Continued)

OTHER PUBLICATIONS

PCT International Search Report in PCT application PCT/CN2011/000787 dated Aug. 11, 2011 with Written Opinion.
PCT International Search Report in PCT application PCT/CN02010/000639 dated Feb. 17, 2011 with Written Opinion.
Schwarzwalder, Wacker-Belsil®—ADM Grades, Silicones for Personal Care, 2004, pp. 1-25.
European Search Report in EP application EP 11 77 7085 dated Aug. 12, 2013.
"Aerosil & Silanes, Versatile and Effective, Degussa", Technical Information, Mar. 2003, pp. 1-21.
Gu, "Preparation and colloidal stability of monodisperse magnetic polymer particles", Journal of Colloid and Interface Science, 2005, vol. 289, pp. 419-426.

(Continued)

*Primary Examiner* — Jessica Worsham
(74) *Attorney, Agent, or Firm* — Foley & Lardner LLP

(57) ABSTRACT

Non-solid skin conditioning compositions comprising 12-hydroxy stearic acid, aminosilicone and water are disclosed. The compositions have a relatively low viscosity and are suitable for spreading on the skin.

15 Claims, No Drawings

(56) References Cited

U.S. PATENT DOCUMENTS

| | | | |
|---|---|---|---|
| 2005/0255134 A1 | 11/2005 | Hasenzahl | |
| 2007/0243220 A1 | 10/2007 | Sandewicz | |
| 2007/0258922 A1 | 11/2007 | Wozniak et al. | |
| 2008/0152681 A1 | 6/2008 | Brown | |
| 2008/0233071 A1 | 9/2008 | Hentrich | |
| 2009/0047225 A1 | 2/2009 | Hasenzahl et al. | |
| 2009/0123410 A1 | 5/2009 | Kuroda et al. | |
| 2009/0232746 A1 | 9/2009 | Mateu | |
| 2009/0317341 A1 | 12/2009 | Madison | |
| 2010/0310617 A1 | 12/2010 | Zhang et al. | |
| 2011/0028412 A1 | 2/2011 | Cappello et al. | |
| 2011/0123579 A1 | 5/2011 | Mohammadi | |
| 2011/0160312 A1* | 6/2011 | Oyama | 514/784 |
| 2013/0041004 A1 | 2/2013 | Drager et al. | |
| 2013/0079419 A1 | 3/2013 | Zhang | |
| 2013/0084243 A1 | 4/2013 | Goetsch et al. | |
| 2013/0096073 A1 | 4/2013 | Sidelman | |
| 2015/0265505 A1 | 9/2015 | Crane et al. | |

FOREIGN PATENT DOCUMENTS

| | | |
|---|---|---|
| CN | 1889921 A | 1/2007 |
| CN | 101087579 | 12/2007 |
| EP | 0117360 | 9/1984 |
| EP | 0129528 A1 | 12/1984 |
| EP | 0327345 | 8/1989 |
| EP | 0455185 A2 | 11/1991 |
| EP | 0751170 | 1/2003 |
| EP | 1380282 A1 | 1/2004 |
| EP | 1579845 A2 | 9/2005 |
| EP | 1618872 | 1/2006 |
| EP | 1618926 | 1/2006 |
| EP | 1671673 | 4/2009 |
| EP | 1671673 B1 | 4/2009 |
| EP | 2269565 A1 | 1/2011 |
| EP | 2280040 A1 | 2/2011 |
| EP | 2319484 | 5/2011 |
| EP | 1905423 B1 | 9/2012 |
| EP | 2543355 A1 | 1/2013 |
| FR | 2860435 | 4/2005 |
| GB | 2431103 A | 4/2007 |
| JP | 56074197 A | 11/1979 |
| JP | 56074197 | 6/1981 |
| JP | 59227999 A | 6/1983 |
| JP | 59277999 | 12/1984 |
| JP | 1163111 | 6/1987 |
| JP | 491010 | 3/1992 |
| JP | 07165542 | 6/1995 |
| JP | 09048962 | 2/1997 |
| JP | 9048962 | 2/1997 |
| JP | 9268118 | 10/1997 |
| JP | 1087431 | 4/1998 |
| JP | 10120525 | 5/1998 |
| JP | 10316550 | 12/1998 |
| JP | 11021222 | 1/1999 |
| JP | 11510522 | 9/1999 |
| JP | 2000204016 | 7/2000 |
| JP | 2002146188 | 5/2002 |
| JP | 2004515513 | 5/2004 |
| JP | 2004250416 | 9/2004 |
| JP | 2007015987 | 1/2007 |
| JP | 2007246453 | 9/2007 |
| JP | 2002068925 | 3/2008 |
| JP | 2008143820 | 6/2008 |
| JP | 2008143821 | 6/2008 |
| JP | 2008222651 A2 | 9/2008 |
| JP | 2008297238 | 12/2008 |
| JP | 2010138110 A | 12/2008 |
| JP | 4266904 B2 | 5/2009 |
| JP | 2009209123 A2 | 9/2009 |
| JP | 2011246352 | 12/2011 |
| WO | WO9531961 | 11/1995 |
| WO | WO9738667 A1 | 10/1997 |
| WO | WO9744049 | 11/1997 |
| WO | WO0029036 | 5/2000 |
| WO | WO0045779 | 8/2000 |
| WO | WO0191704 | 12/2001 |
| WO | WO03105788 A2 | 12/2003 |
| WO | WO2005053633 | 6/2005 |
| WO | WO2006056283 A1 | 6/2006 |
| WO | WO2006106366 A1 | 10/2006 |
| WO | WO2007058380 A1 | 5/2007 |
| WO | WO2007130777 | 11/2007 |
| WO | WO2009032096 | 5/2009 |
| WO | WO2009059869 | 5/2009 |
| WO | WO2009082565 A1 | 7/2009 |
| WO | WO2009090114 | 7/2009 |
| WO | WO2009111128 | 9/2009 |
| WO | WO2009149879 A1 | 12/2009 |
| WO | WO2009153169 A1 | 12/2009 |
| WO | WO2010063952 | 6/2010 |
| WO | WO2010121924 A1 | 10/2010 |
| WO | WO2010135237 | 11/2010 |
| WO | WO2011005623 A1 | 1/2011 |
| WO | WO2011/018369 A2 | 2/2011 |
| WO | WO2011056547 A1 | 5/2011 |
| WO | WO2011056623 A1 | 5/2011 |
| WO | WO2011108491 A1 | 9/2011 |
| WO | WO2011137563 A1 | 11/2011 |
| WO | WO2011137664 A1 | 11/2011 |
| WO | WO2011138445 A1 | 11/2011 |
| WO | WO2011154314 A2 | 12/2011 |
| WO | WO2012061025 A1 | 5/2012 |
| WO | WO2013064365 | 5/2013 |
| WO | WO2013064367 | 5/2013 |
| WO | WO2013064596 | 5/2013 |
| WO | WO2013064597 | 5/2013 |
| WO | WO2013064598 | 5/2013 |
| WO | WO2013064599 A1 | 5/2013 |

OTHER PUBLICATIONS

Emmert, "Quantification of the Soft-Focus Effect", Cosmetics and Toiletries Magazine, Jul. 1996, vol. 111, pp. 57-61.
"Fumed Silica and Fumed Alumina in Coatings Applications", Fumed Metal Oxides, Cabot Corporation 2008, pp. 1-11; p. 1 to p. 20.
IPRP2 in PCTEP2011057333 dated Sep. 11, 2012; p. 21 to p. 34.
European Search Report in EP12156114, dated Jul. 26, 2012; p. 35 to p. 36.
European Search Report in EP12156115, dated Jul. 25, 2012; p. 37 to p. 38.
PCT Search Report in PCT/EP2012/070485 dated, Mar. 15, 2013 pp. 1-4; p. 39 to p. 42.
PCT Search Report in PCT/EP2012/070491 dated Apr. 10, 2014, pp. 1-4; p. 43 to p. 46.
PCT Search Report in PCTCN2010000639 dated Feb. 17, 2011; p. 47 to p. 50.
PCT Search Report in PCTEP2011057333 dated Oct. 27, 2011; p. 51 to p. 53.
Vold et al., "Dispersion of Alkylammonium Montmorillonites in Organic Liquids", Journal of Colloid Science, Aug. 1, 1962, pp. 589-600, vol. 17, Issue 6; p. 54 to p. 65.
Written Opinion in PCTCN2010000639 dated Feb. 17, 2011; p. 66 to p. 70.
Written Opinion1 in PCTEP2011057333 dated Jul. 27, 2012; p. 71 to p. 74.
Written Opinion2 in PCTEP2011057333 dated Oct. 27, 2011; p. 75 to p. 80.
Written Opinion3 in PCTEP2011057333 dated Jun. 18, 2012; p. 81 to p. 84.
IPRP1 in PCTEP2012071659 dated May 6, 2014. pp. 1 to 7.
IPRP1 in PCTEP2012071660 dated May 6, 2014. pp. 8 to 15.
IPRP1 in PCTEP2012071661 dated May 6, 2014. pp. 16 to 23.
IPRP1 in PCTEP2012071662 dated May 6, 2014. pp. 24 to 30.
IPRP2 in PCTCN2011000787 dated Aug. 16, 2012. pp. 31 to 35.
IPRP2 in PCTEP2012070485 dated Nov. 29, 2013. pp. 36 to 41.
IPRP2 in PCTEP2012070491 dated Jan. 21, 2014. pp. 42 to 48.
Search Report in EP12157745 dated Jan. 31, 2013. pp. 1 to 2.
Search Report in EP12157746 dated Jan. 31, 2013. pp. 3 to 4.
Search Report in EP12157747 dated Feb. 5, 2013. pp. 5 to 6.

(56) References Cited

OTHER PUBLICATIONS

Search Report in EP12157748 dated Feb. 6, 2013. pp. 7 to 8.
Search Report in PCTCN2011081800 dated Aug. 9, 2012. pp. 1 to 4.
Search Report in PCTEP2012071659 dated Mar. 15, 2013. pp. 5 to 7.
Search Report in PCTEP2012071660 dated May 29, 2013. pp. 8 to 11.
Search Report in PCTEP2012071661 dated May 29, 2013. pp. 12 to 15.
Search Report in PCTEP2012071662 dated Mar. 15, 2013. pp. 16 to 18.
Written Opinion in EP11777085 dated Aug. 26, 2013. pp. 1 to 2.
Written Opinion in EP12156114 dated Jul. 26, 2012. pp. 3 to 5.
Written Opinion in EP12156115 dated Jul. 25, 2012. pp. 6 to 8.
Written Opinion in EP12157745 dated Jan. 31, 2013. pp. 9 to 11.
Written Opinion in EP12157746 dated Jan. 31, 2013. pp. 12 to 13.
Written Opinion in EP12157747 dated Feb. 5, 2013. pp. 14 to 16.
Written Opinion in EP12157748 dated Feb. 6, 2013. pp. 17 to 19.
Written Opinion in PCTCN2011081800 dated Aug. 9, 2012. pp. 1 to 4.
Written Opinion in PCTEP2012070491 dated Apr. 10, 2013. pp. 5 to 11.
Written Opinion in PCTEP2012071659 dated Mar. 15, 2013. pp. 12 to 18.
Written Opinion in PCTEP2012071660 dated May 29, 2013. pp. 19 to 26.
Written Opinion in PCTEP2012071661 dated May 29, 2013. pp. 27 to 34.
Written Opinion in PCTEP2012071662 dated Mar. 15, 2013. pages to.
Written Opinion1 in PCTEP2012070485 dated Mar. 15, 2013. pp. 42 to 49.
Written Opinion2 in PCTEP2012070485 dated Mar. 15, 2013. pp. 50 to 56.
Co-pending Application: Applicant: Zhang et al., U.S. Appl. No. 13/695,439, filed Dec. 4, 2012.
Co-pending Application: Applicant: Khoshdel et al., U.S. Appl. No. 14/354,604, filed Apr. 28, 2014.
Co-pending Application: Applicant: Khoshdel et al., U.S. Appl. No. 14/354,603, filed Apr. 28, 2014.
Aerosil R812 S Safety Data Sheet and Product Sheet, Evonik Industries, Jun. 24, 2010, 1-7, www.stobec.com.
Microspheres, Jun. 9, 2014, pp. 1-2, www.koboproductsinc.com.
Written Opinion in EP1719805 dated Apr. 28, 2015.
Amodimethicone, Saapedia, May 21, 2015, pp. 1-3; "www.saapedia.org/en/saa/?type-detail&id-1885". pp. 1 to 3.
Aerosil® R812S Product Sheet, Dec. 2, 2014, p. 1; "www.aerosil.com/lpa-productfinder/page/productsbytext/detail.html?pid=1832". pp. 4 to 4.
Postiaux et al., "Soft focus of silica silylate aerogel", Research Disclosure, 2007, vol. 516 No. 5, p. 347; XP007137202. pp. 5 to 7.
Written Opinion in EP12775014 dated Jul. 9, 2015. pp. 8 to 12.
Hasenzahl et al., "Fumed Silica for Personal Care and Cosmetics-versatile and effective", SOFW International Journal, 2003, vol. 129, pp. 1-8; XP002292235.
Sharmani, "The Role of Vitamin B3 (Niacinamide) in Skin Care", Pharmacymix.com, Skin Care Pharmacy and Blog Specializing in Anthelios and Mexoryl Sunscreens, 2008, pp. 1-2.
Sharmani, The Role of Vitamin B3 (Niacinamide) in Skin Care, The Role of Vitamin B3 (Niacinamide) Pharmacymix Dec. 7, 2008 p. 1-2, Dec. 7. 2008, 1-2, . . . , US.
Silica Silylate, EWG's Skin Deep Cosmetics Database, 2016, pp. 1-2, http://www.ewg.org/skindeep/ingredient/705921/SILICA__SILYLATE/,.
Bergfeld, et al., Safety Assessment of Dimethicone Crosspolymers as Used in Cosmetics, Cosmetic Ingredient Review, Sep. 28, 2012, pp. 1-62.
Unknown, Synthetic Amorphous Silica, European Centre for Ecotoxicology and Toxicology of Chemicals 2002, 2002, pp. 1-237, relevant page: P38; http://members.ecetoc.org/Documents/Document/JACC%20051.pdf, ISSN-0773-6339-51; JACC No. 51.

\* cited by examiner

SKIN CONDITIONING COMPOSITIONS CONTAINING 12-HYDROXYSTEARIC ACID

BACKGROUND OF THE INVENTION

Salts of 12-hydroxystearic acid, i.e. soaps, have been described in wash-off body cleansing compositions (JP 4,266,904; JP 59/227,999, JP 56/074,197). 12-hydroxystearic acid (hereinafter "12HSA") is reported to have a wide variety of beneficial cosmetic effects on skin, e.g. it is a known PPAR-alpha (peroxisome proliferator activated receptors sub-type alpha) activator, and a sebum secretion inhibitor. See e.g. Alaluf et al. U.S. Pat. No. 6,423,325, Mayes et al. U.S. Pat. No. 6,713,051, WO2006/056283 (Hindustan Lever), Minami et al. U.S. Pat. No. 6,197,343, Granger et al. US2004/0043044. Madison US 2009/0317341 describes 12HSA as a skin lightening agent. As such, skin conditioning products obtaining 12HSA are highly desirable. JP 09-048962 describes the use of 12HSA or its salt as an effective constituent of a solidification inhibitor, to inhibit solidification of a liquid detergent or a liquid cosmetic; all the examples containing a fully neutralized salt of 12HSA. Unfortunately, 12HSA is a solid and has no water solubility and limited oil solubility. Indeed, 12HSA has traditionally been used as gelling agent e.g. in lipsticks and anti-perspirant stick compositions. See also EP 0129528, U.S. Pat. No. 6,680,285, Abbas et al. U.S. Pat. No. 6,680,285, Tanner et al. U.S. Pat. No. 5,759,524, WO95/31961 (Procter & Gamble), Kawa et al., US 2004/0044078 (describing the use of 12HSA to increase viscosity of cosmetic compositions), and JP 2010/138,110. Salts of 12HSA are only marginally more water-soluble. Thus, non-solid skin conditioning compositions containing 12HSA are highly desirable.

SUMMARY OF THE INVENTION

The invention includes non-solid skin conditioning composition comprising:
  (a) from about 0.01 to about 15% by weight of the composition of 12-hydroxystearic acid;
  (b) an aminosilicone wherein the weight ratio of the aminosilicone to the 12-hydroxystearic acid is at least about 2:1;
  (c) from about 1 to about 99% by weight of the composition of water; wherein when the water amount is greater than 20% by weight of the composition the composition further comprises a particle having an isoelectric point below the pH of the composition;
wherein the viscosity of the composition is in the range of from about 1 Pas to about 500 Pas.

According to the present invention, non-solid skin conditioning compositions have been prepared that contain 12HSA and water, wherein 12HSA remains in non-solid, non-crystallized form. Keeping 12HSA in non-crystallized form is crucial, to prevent solidifying of the product on storage, or upon spreading on the skin, rendering it unusable and/or not bioavailable.

In another aspect, the invention also includes an additive composition for skin conditioning composition comprising:
  (a) from about 0.01 to about 15% by weight of the composition of 12-hydroxystearic acid; and
  (b) an aminosilicone where the weight ratio of the aminosilicone to the 12-hydroxystearic acid is at least about 2:1.

This non-solid additive contains 12HSA in a substantially non-crystallized form. The additive may be employed in the skin conditioning compositions.

The invention also includes methods of making and using the compositions.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

"Conditioning" as used herein means prevention and treatment of dry skin, acne, photo-damaged skin, appearance of wrinkles, age spots, aged skin, increasing stratum corneum flexibility, lightening skin color, controlling sebum excretion and generally increasing the quality of skin. The composition may be used to improve skin desquamation and epidermal differentiation and improve skin appearance or general aesthetics.

"Leave-on" as used herein means compositions that are applied to the skin and are not intended to be washed or rinsed off for some period of time, as contrasted with cleansing or wash-off or rinse-off compositions.

"Non-solid" as used herein means that the composition has a measurable viscosity (measurable for instance with a Brookfield Viscometer DV-I+(20 RPM, RV6, 30 Seconds, 25° C.) in the range of from 1 Pas to 500 Pas, preferably from 2 Pas to 100 Pas, more preferably from 3 Pas to 50 Pas.

"Non-crystallized" as used herein means that the composition is substantially free of 12HSA crystals or solids, specifically contains less than 10% by weight of total 12HSA, of 12HSA crystals, preferably less than 5%, most preferably less than 2%. The presence or absence of the 12HSA crystals is verified by viewing a sample of the composition through an optical microscope fitted with cross-polarizers at a magnification of 10×. A Leitz Laborlux 12 Pol S optical microscope was used in the present invention.

12HSA

The inventive compositions include 12HSA. As used herein, 12HSA is meant to include the acid, its salts and its esters. Preferably, the compositions typically contain at least 40% of the total 12HSA in its acid form, preferably at least 50%, more preferably at least 60% in order to optimize bioavailability, and therefore efficacy. As with other fatty acids the apparent pKa for 12HSA is expected to be greater than 8. At the pKa, the fatty acid will exist as 50% soap and 50% acid. Therefore, preferably the pH of the inventive compositions is less than about 8, more preferably is in the range of from 3.5 to 8.0, most preferably is from 5 to 7.8. 12HSA is included in the inventive compositions in an amount of from 0.01 to 15%, preferably from 0.1 to 12%, more preferably from 0.5 to 10%, and optimally from 1 to 5%. The amounts of 12HSA herein include both acid and salt amounts. The amounts of 12HSA or salts thereof are not meant to be included within the surfactants amounts herein.

Aminosilicone

The aminosilicones useful in the present invention include primary, secondary and tertiary amines. Preferably the aminosilicones have a general Formula I as follows:

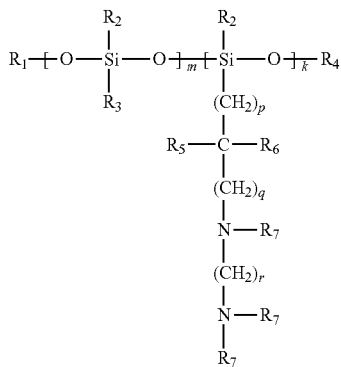

wherein:

m=5-1,000,000; preferably 10-500,000; more preferably 20-300,000; most preferably 50-100,000.

k=1-50; preferably 2-40; more preferably 3-30, most preferably 5-20 p, q and r are independently in the range of 1-30; preferably 1-20; more preferably 1-10; most preferably 1-4

$R_1$ and $R_4$ are independently $C_nH_{2n+1}$; wherein n=1-30; preferably 1-25; more preferably 1-20; most preferably 1-12

$R_2$, $R_3$ and $R_6$ are independently selected from aryl radicals such as phenyl and naphthyl; arylalkyl radicals such as benzyl and naphthyl, and alkyl radicals, namely $C_nH_{2n+1}$. The preferred $R_2$ and $R_3$ groups are phenyl radicals. More preferred $R_2$ and $R_3$ groups are alkyl radicals, wherein n=1-20; preferably 1-10; more preferably 1-5; most preferably 1-2.

$R_5$ is a hydrogen, and or alkyl an radical, namely $C_nH_{2n+1}$, wherein, n=1-10-, preferably 1-5, more preferably 1-2. Most preferred $R_5$ is a hydrogen radical.

$R_7$ is selected from the group consisting of hydrogen, alkyl radicals as above, polyol radicals such as ethyleneglycol, propylene glycol, polyethylene glycols, polypropylene glycols, preferably a polyol radical. Most preferred polyol radical is

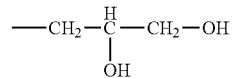

The most preferred example of a particularly suitable aminosilicone has Formula 2 as follows:

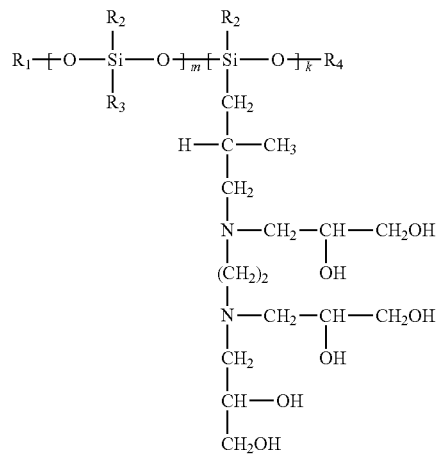

wherein:

m, k and $R_1$-$R_4$ are as defined above.

Another suitable aminosilicone has Formula 3 as follows:

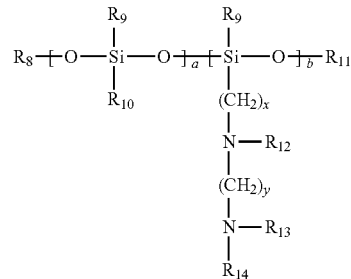

wherein:

a=5-1,000,000; preferably 10-500,000; more preferably 20-300,000; most preferably 50-100,000.

b=1-50; preferably 2-40; more preferably 3-30, most preferably 5-20;

x and y=1-10, preferably 1-8, more preferably 1-6 and most preferably 1-4;

$R_8$, $R_9$ and $R_{10}$ are independently selected from alkyl radicals, namely $C_nH_{2n+1})_3$, wherein n=1-20; preferably 1-10; more preferably 1-5; most preferably 1-2

$R_{11}$=a tertiary alkyl radical such as —$C(C_nH_{2n+1})_3$, wherein n=1-10, preferably 1-5, more preferably 1-3 and most preferably 1-2

$R_{12}$, $R_{13}$ and $R_{14}$ are independently selected from the group consisting of hydrogen, and or alkyl radicals, namely $C_nH_{2+1}$, wherein, n=1-10-, preferably 1-5, more preferably 1-2. Most preferred $R_{12}$, $R_{13}$ and $R_{14}$ are hydrogen radicals.

Another suitable example of aminosilicone has Formula 4 as follows:

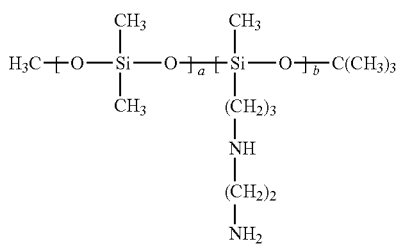

wherein a and b are as defined as above.

The aminosilicones suitable for use in the present invention are commercially available, e.g. from Dow or Wacker Chemical.

According to the present invention, in order to maintain the 12HSA in the substantially non-crystallized, non-solid, form in the composition, the weight ratio of the aminosilicone to 12HSA should be at least 2:1, preferably is in the range of from 2:1 to 100:1, more preferably in the range of from 3:1 to 75:1, and most preferably is in the range of from 3:1 to 20:1.

Water

The additive compositions of the present invention may be prepared in the absence of water, although water may still be included. The skin conditioning non-additive compositions of the present invention include water. The compositions of the present invention include water generally in the range from 1 to 99% water, preferably from 20 to 98%, most preferably from 30 to 90%, optimally from 35 to 80% of water.

Particle

When the water content in the inventive emulsions exceeds 20%, by weight of the composition, the compositions need to include a particle having an isoelectric point below the pH of the composition. Typically, the particle has an isoelectric point under 11, and preferably, under 7.5.

Illustrative yet non-limiting examples of the type of particle that may be used in this invention include oxides of silicon, zinc, iron, cerium, zirconium, titanium or aluminum, as well as stearates of zinc, magnesium, or calcium, including any mixtures thereof or the like. Still other particles suitable for use include metal silicates like calcium and/or magnesium silicate whereby the same may be used alone or in combination with any of the particles described herein.

In a preferred embodiment, particle used in this invention comprises at least 0.1% by weight silicon dioxide (i.e., silica), and preferably, at least 25% by weight silicon dioxide, and most preferably, at least 50% to 100% by weight silicon dioxide, based on total weight of particle in the emulsion and including all ranges subsumed therein. In an often preferred embodiment, the particle used is silica, especially pyrogenically produced silica comprising at least one of the following groups:

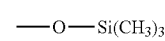 (I)

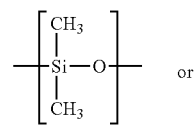 or (II)

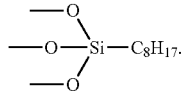 (III)

Such silicas are described in U.S. Pat. No. 7,282,236 and made commercially available from suppliers like Evonik Degussa GmbH under the names Aerosil R812, R8128, R202, MS202 and R805. Silica of the octylsilane type and comprising the group represented by formula III is sold under the name Aerosil R805 and is especially preferred.

The emulsion of the present invention often comprises from 0.25 to 45%, and preferably, from about 1 to 25%, and most preferably, from 1.5 to 15% by weight particle, based on total weight of the emulsion.

The particle used typically has a diameter of less than three microns, and preferably, less than two microns, and most preferably, from 10 nm to 1.5 microns, including all ranges subsumed therein.

Additive Composition

The additive composition of the invention comprises 12HSA and the aminosilicone, as described above. The additive composition is non-solid and comprises 12HSA in substantially non-crystallized form. The additive composition may include water, and then it follows the same rules for optional inclusion of the particle at water amounts of more than 20%, as discussed above. The additive composition may be used as a pre-mix for skin conditioning composition, or it may be marketed as a separate composition.

Optional Ingredients

Compositions of the invention may include carriers in addition to water. Among the useful additional carriers are emollients, fatty acids, fatty alcohols, thickeners and combinations thereof.

Emollient materials may serve as cosmetically acceptable carriers. These may be in the form of silicone oils, natural or synthetic esters, hydrocarbons, alcohols and fatty acids. Amounts of the emollients may range anywhere from about 0.1 to about 95%, preferably between about 1 and about 50% by weight of the composition.

Silicone oils may be divided into the volatile and non-volatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 5 to 6, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to 0.1 m$^2$/s at 25° C. Among the preferred nonvolatile emollients useful in the present compositions are the polydimethyl siloxanes having viscosities from about $1 \times 10^{-5}$ to about $4 \times 10^{-4}$ m$^2$/s at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:
a) Alkyl esters of saturated fatty acids having 10 to 24 carbon atoms. Examples thereof include behenyl neopentanoate, isononyl isonanonoate, isopropyl myristate and octyl stearate.
b) Ether-esters such as fatty acid esters of ethoxylated saturated fatty alcohols.
c) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.
d) Wax esters such as beeswax, spermaceti wax and tribehenin wax.
e) Sugar ester of fatty acids such as sucrose polybehenate and sucrose polycottonseedate.

Natural ester emollients principally are based upon mono-, di- and tri-glycerides. Representative glycerides include sunflower seed oil, cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from about 0.1 to about 20% by weight of the compositions.

Hydrocarbons which are suitable cosmetically acceptable carriers include petrolatum, mineral oil, $C_{11}$-$C_{13}$ isoparaffins, polybutenes and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, linoleic, linolenic, hydroxystearic and behenic acids and mixtures thereof.

Fatty alcohols having from 10 to 30 carbon atoms are another useful category of cosmetically acceptable carrier. Illustrative of this category are stearyl alcohol, lauryl alcohol, myristyl alcohol, oleyl alcohol and cetyl alcohol and mixtures thereof.

Thickeners can be utilized as part of the cosmetically acceptable carrier of compositions according to the present invention. Typical thickeners include crosslinked acrylates (e.g. Carbopol 982®), hydrophobically-modified acrylates (e.g. Carbopol 1382®), polyacrylamides (e.g. Sepigel 305®), acryloylmethylpropane sulfonic acid/salt polymers and copolymers (e.g. Aristoflex HMB® and AVC®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Inorganics may also be utilized as thickeners, particularly clays such as bentonites and hectorites, fumed silicas, talc, calcium carbonate and silicates such as magnesium aluminum silicate (Veegum®). Amounts of the thickener may range from 0.0001 to 10%, usually from 0.001 to 1%, optimally from 0.01 to 0.5% by weight of the composition.

Preferred are emollients that can be used, especially for products intended to be applied to the face, to improve sensory properties and are chosen from the group of oils that do not form stiff gels with 12HSA; these include polypropylene glycol-14 butyl ether otherwise known as Tegosoft PBE, or PPG15 stearyl ether such as Tegosoft E, other oils such as esters, specifically, isopropyl myristate, isopropyl palmitate, other oils could include castor oils and derivatives thereof.

Humectants of the polyhydric alcohol-type can be employed as cosmetically acceptable carriers. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 15% by weight of the composition.

Skin moisturizers, e.g. hyaluronic acid and/or its precursor N-acetyl glucosamine may be included. N-acetyl glucosamine may be found in shark cartilage or shitake mushrooms and are available commercially from Maypro Industries, Inc (New York). Other preferred moisturizing agents include hydroxypropyl tri($C_1$-$C_3$ alkyl)ammonium salts. These salts may be obtained in a variety of synthetic procedures, most particularly by hydrolysis of chlorohydroxypropyl tri($C_1$-$C_3$ alkyl)ammonium salts. A most preferred species is 1,2-dihydroxypropyltrimonium chloride, wherein the $C_1$-$C_3$ alkyl is a methyl group. Amounts of the salt may range from about 0.2 to about 30%, and preferably from about 0.5 to about 20%, optimally from about 1% to about 12% by weight of the topical composition, including all ranges subsumed therein.

Ordinarily the $C_1$-$C_3$ alkyl constituent on the quaternized ammonium group will be methyl, ethyl, n-propyl, isopropyl or hydroxyethyl and mixtures thereof. Particularly preferred is a trimethyl ammonium group known through INCI nomenclature as a "trimonium" group. Any anion can be used in the quat salt. The anion may be organic or inorganic with proviso that the material is cosmetically acceptable. Typical inorganic anions are halides, sulfates, phosphates, nitrates and borates. Most preferred are the halides, especially chloride. Organic anionic counter ions include methosulfate, toluoyl sulfate, acetate, citrate, tartrate, lactate, gluconate, and benzenesulfonate.

Still other preferred moisturizing agents which may be used, especially in conjunction with the aforementioned ammonium salts include substituted urea like hydroxymethyl urea, hydroxyethyl urea, hydroxypropyl urea; bis(hydroxymethyl) urea; bis(hydroxyethyl) urea; bis(hydroxypropyl) urea; N,N'-dihydroxymethyl urea; N,N'-dihydroxyethyl urea; N,N'-di-hydroxypropyl urea; N,N,N'-trihydroxyethyl urea; tetra(hydroxymethyl) urea; tetra(hydroxyethyl) urea; tetra(hydroxypropyl urea; N-methyl, N'-hydroxyethyl urea; N-ethyl-N'-hydroxyethyl urea; N-hydroxypropyl-N'-hydroxyethyl urea and N,N' dimethyl-N-hydroxyethyl urea. Where the term hydroxypropyl appears, the meaning is generic for either 3-hydroxy-n-propyl, 2-hydroxy-n-propyl, 3-hydroxy-1-propyl or 2-hydroxy-1-propyl radicals. Most preferred is hydroxyethyl urea. The latter is available as a 50% aqueous liquid from the National Starch & Chemical Division of ICI under the trademark Hydrovance.

Amounts of substituted urea that may be used in the topical composition of this invention range from about 0.01 to about 20%, and preferably, from about 0.5 to about 15%, and most preferably, from about 2 to about 10% based on total weight of the composition and including all ranges subsumed therein.

When ammonium salt, and substituted urea are used, in a most especially preferred embodiment at least from about 0.01 to about 25%, and preferably, from about 0.2 to about 20%, and most preferably, from about 1 to about 15% humectant, like glycerine, is used, based on total weight of the topical composition and including all ranges subsumed therein.

Form of the Composition

The compositions of the present invention are non-solid, and may be rinse-off or leave-on. Leave-on compositions are preferred because the virtue of 12HSA remaining substantially non-crystallized after being spread on the skin is particularly in the inventive compositions is particularly advantageous. Essentially, the "non-solidness" of the composition means that the viscosity of the compositions, e.g. as measured using a Brookfield DV-I+ viscometer (20 RPM, RV6, 30 seconds, 25° C.). The viscosity is in general in the range of from 1 Pas to 500 Pas, preferably from 1 Pas to 200 Pas, more preferably from 2 Pas to 100 Pas, most preferably from 3 Pas to 50 Pas.

The preferred compositions of the present invention are leave-on compositions and are intended to be applied to remain on the skin. These leave-on compositions are to be distinguished from compositions which are applied to the skin and subsequently removed either by washing, rinsing, wiping, or the like either after or during the application of the product. Surfactants typically used for rinse-off compositions have physico-chemical properties giving them the ability to generate foam/lather in-use with ease of rinse; they can consist of mixtures of anionic, cationic, amphoteric, and nonionic. Surfactants used in leave-on compositions on the other hand are not required to have such properties. Rather, as leave-on compositions are not intended to be rinsed-off they need to be non-irritating and therefore it would be necessary to minimize the total level of surfactant and the total level of anionic surfactant in leave-on compositions. Therefore, the preferred leave-on compositions of the present invention contain, with respect to surfactants, predominantly nonionic surfactants. The anionic surfactants are present in an amount of at most 5%, preferably from 0.01 to 4%, more preferably from 0.01 to 3%, most preferably from 0.01 to 2% and optimally are substantially absent (less than 1%, preferably less than 0.1%, or even less than 0.01%). Salts of 12HSA are not considered anionic surfactants herein. The total level of surfactant in the inventive compositions is preferably no more than 10%, more preferably below 8%, most preferably at most 5%.

The compositions of the present invention are typically in the form of emulsions, which may be oil-in-water (including high internal phase emulsions), or water-in-oil; preferably the compositions are oil-in-water emulsions.

Surfactants

It is preferred that the inventive composition is substantially free of surfactant, i.e contains at most 2%, i.e. from 0.0001 to 2%, preferably less 1% surfactant, most preferably less than 0.1%, for reasons described immediately above. One of the virtues of the present invention is that it is possible to make emulsions, including high water content emulsions, in the substantial absence of surfactant. But surfactant can optionally be added. Total concentration of the surfactant when present may range from about 0.1 to about 20%, preferably from about 1 to about 10%, optimally from about 1 to about 5% by weight of the composition, and being highly dependent upon the type of personal care product. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) and trialkylamine oxides are also suitable nonionic surfactants.

Useful amphoteric surfactants include cocoamidopropyl betaine, $C_{12}$-$C_{20}$ trialkyl betaines, sodium lauroamphoacetate, and sodium laurodiamphoacetate.

Preferred anionic surfactants include soap, alkyl ether sulfates and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, $C_8$-$C_{20}$ sarcosinates, $C_8$-$C_{20}$ acyl lactylates, sulfoacetates and combinations thereof.

Rheology Modifier

A rheology modifier may be included and is selected from the group consisting of silica such as fumed silica or hydrophilic silicas and clays such as magnesium aluminum silicate, betonites, hectorite, laponite, and mixtures thereof. A rheology modifier is employed in an amount of from 0.01 to 2%, preferably from 0.05 to 1%.

Skin Benefit Ingredients

The inventive composition preferably includes an additional skin lightening compound (in addition to 12HSA), to obtain optimum skin lightening performance at an optimum cost. Illustrative substances are placental extract, lactic acid, niacinamide, arbutin, kojic acid, ferulic acid, hydroquinone, resorcinol and derivatives including 4-substituted resorcinols and combinations thereof. More preferably, such additional skin lightening compound is a tyrosinase inhibitor, to complement the melanogenesis inhibition activity of the substituted monoamines, most preferably a compound selected from the group consisting of kojic acid, hydroquinone and 4-substituted resorcinol. Also, dicarboxylic acids represented by the formula HOOC—(CxHy)-COOH where x=4 to 20 and y=6 to 40 such as azelaic acid, sebacic acid, oxalic acid, succinic acid, fumaric acid, octadecenedioic acid or their salts or a mixture thereof, most preferably fumaric acid or salt thereof, especially di-sodium salt. It has been found that combination of 12HSA with fumaric acid or salts thereof are particularly preferred, especially for skin lightening formulations. Amounts of these agents may range from about 0.1 to about 10%, preferably from about 0.5 to about 2% by weight of the composition. It is preferred that the skin lightening coactive according to the invention is vitamin B3 or a derivative thereof and is selected from the group consisting of niacinamide, nicotinic acid esters, non-vasodilating esters of nicotinic acid, nicotinyl amino acids, nicotinyl alcohol esters of carboxylic acids, nicotinic acid N-oxide, niacinamide N-oxide and mixtures thereof.

Sunscreen is another preferred ingredient of the inventive compositions. Particularly preferred are such materials as ethylhexyl p-methoxycinnamate (available as Parsol MCX®), Avobenzene (available as Parsol 1789®), octylsalicylate (available as Dermablock OS®), tetraphthalylidene dicamphor sulfonic acid (available as Mexoryl SX®), benzophenone-4 and benzophenone-3 (Oxybenzone). Inorganic sunscreen actives may be employed such as microfine titanium dioxide, zinc oxide, polyethylene and various other polymers. By the term "microfine" is meant particles of average size ranging from about 10 to about 200 nm, preferably from about 20 to about 100 nm. Amounts of the sunscreen agents when present may generally range from 0.1 to 30%, preferably from 2 to 20%, optimally from 4 to 10% by weight of the composition.

More preferred inventive compositions include additional skin lightening compound, especially tyrosinase inhibitor, and a sunscreen compound.

Another preferred ingredient of the inventive compositions is a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$-$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. No. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and U.S. Pat. No. Reissue 34,075, issued Sep. 22, 1992 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). Preferred retinoids are retinol, retinyl palmitate, retinyl acetate, retinyl propionate, retinal and combinations thereof. The retinoid is preferably substantially pure, more preferably essentially pure. The compositions of this invention may contain a safe and effective amount of the retinoid, such that the resultant composition is safe and effective for regulating keratinous tissue condition, preferably for regulating visible and/or tactile discontinuities in skin, more preferably for regulating signs of skin aging, even more preferably for regulating visible and/or tactile discontinuities in skin texture associated with skin aging. The compositions preferably contain from or about 0.005% to or about 2%, more preferably 0.01% to or about 2%, retinoid. Retinol is preferably used in an amount of from or about 0.01% to or about 0.15%; retinol esters are preferably used in an amount of from or about 0.01% to or about 2% (e.g., about 1%); retinoic acids are preferably used in an amount of from or about 0.01% to or about 0.25%; tocopheryl-retinoate, adapalene, and tazarotene are preferably used in an amount of from or about 0.01% to or about 2%.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may include vitamins. Illustrative vitamins are Vitamin A (retinol), Vitamin $B_2$, Vitamin $B_3$ (niacinamide), Vitamin $B_6$, Vitamin B12, Vitamin C, Vitamin D, Vitamin E, Vitamin K and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. A particularly suitable Vitamin $B_6$ derivative is Pyridoxine Palmitate. Flavonoids may also be useful, particularly glucosyl hesperidin, rutin, and soy isoflavones (including genistein, daidzein, equol, and their glucosyl derivatives) and mixtures thereof. Total amount of vitamins or flavonoids when present may range from 0.0001 to 10%, preferably from 0.01% to 1%, optimally from 0.1 to 0.5% by weight of the composition.

Another type of useful substance can be that of an enzyme such as oxidases, proteases, lipases and combinations. Particularly preferred is superoxide dismutase, commercially available as Biocell SOD from the Brooks Company, USA.

Desquamation promoters may be present. Illustrative are the monocarboxylic acids. Monocarboxylic acids may be substituted or unsubstituted with a carbon chain length of up to 16. Particularly preferred carboxylic acids are the alpha-hydroxycarboxylic acids, beta-hydroxycarboxylic or poly-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic malic and tartaric acids. A representative salt that is particularly preferred is ammonium lactate. Salicylic acid is representative of the beta-hydroxycarboxylic acids. Amounts of these materials when present may range from about 0.01 to about 15% by weight of the composition. Other phenolic acids include ferulic acid, salicylic acid, kojic acid and their salts.

A variety of herbal extracts may optionally be included in compositions of this invention. Illustrative are pomegranate, white birch (*Betula Alba*), green tea, chamomile, licorice and extract combinations thereof. The extracts may either be water soluble or water-insoluble carried in a solvent which respectively is hydrophilic or hydrophobic. Water and ethanol are the preferred extract solvents.

Also included may be such materials as resveratrol, alpha-lipoic acid, ellagic acid, kinetin, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B, Ceramide 6 and Ceramide 7) as well as pseudoceramides may also be utilized for many compositions of the present invention but may also be excluded. Amounts of these materials may range from about 0.000001 to about 10%, preferably from about 0.0001 to about 1% by weight of the composition.

Colorants, opacifiers and abrasives may also be included in compositions of the present invention. Each of these substances may range from about 0.05 to about 5%, preferably between 0.1 and 3% by weight of the composition.

The compositions of the present invention may contain a safe and effective amount of a peptide active selected from pentapeptides, derivatives of pentapeptides, and mixtures thereof. As used herein, "pentapeptides" refers to both the naturally occurring pentapeptides and synthesized pentapeptides. Also useful herein are naturally occurring and commercially available compositions that contain pentapeptides. A preferred commercially available pentapeptide derivative-containing composition is Matrixyl™, which is commercially available from Sederma, France. The pentapeptides and/or pentapeptide derivatives are preferably included in amounts of from about 0.000001% to about 10%, more preferably from about 0.000001% to about 0.1%, even more preferably from about 0.00001% to about 0.01%, by weight of the composition. In embodiments wherein the pentapeptide-containing composition, Matrixyl™, is used, the resulting composition preferably contains from about 0.01% to about 50%, more preferably from about 0.05% to about 20%, and even more preferably from about 0.1% to about 10%, by weight of the resulting composition, of Matrixyl™.

Additional peptides, including but not limited to, di-, tri-, and tetrapeptides and derivatives thereof, and poly amino acid sequences of molecular weight from 200-20000. Amino acids may be naturally occurring or synthetic, dextro or levo, straight chain or cyclized and may be included in the compositions of the present invention in amounts that are safe and effective. As used herein, "peptides" refers to both the naturally occurring peptides and synthesized peptides. Also useful herein are naturally occurring and commercially available compositions that contain peptides.

Suitable dipeptides for use herein include Carnosine. Preferred tripeptides and derivatives thereof may be purchased as Biopeptide CL™ and a copper derivative sold commercially as lamin, from Sigma (St. Louis, Mo.).

Further ingredients useful in skin care compositions herein may be selected from any and all: skin conditioning agents, skin feel mildness agents, suspending agents, auxiliary thickening agents, viscosity control agents, dispersants, solubilizing/clarifying agents, stabilizers, opacifiers/pearlescent agents, chelating/sequestering agents, hydrotropes, bactericides/fungicides, antioxidants, pH control agents, buffering agents, colorants and perfumes/fragrances, water, other optional ingredients (auxiliary agents) and the like.

The compositions of the present invention can also be optionally, incorporated into a water insoluble substrate for application to the skin such as in the form of a treated wipe.

Method of Making Compositions

Compositions within the scope of this invention are preferably prepared in the following manner. Mix all water soluble ingredients including preservatives, thickening polymer, optionally glycerine, and water and heat to a temperature of 70-90° C. In a separate vessel mix all oil soluble ingredients including 12HSA, optional particle (e.g. silica) and optionally surfactants to a temperature of 70-90° C. Mix the oil phase and the water phase at a temperature of 70-90° C. with agitation. Optionally, add niacinamide at 45° C. followed by addition of fragrance and phenoxyethanol at 40° C. Cool the mixture to room temperature with mixing.

Method of Using Compositions

The composition according to the invention is intended primarily as a product for topical application to human skin, especially as an agent for conditioning and smoothening the skin, and preventing or reducing the appearance of wrinkled or aged skin, or age spots, or lightening of the skin.

In use, a small quantity of the composition, for example from 1 to 5 ml, is applied to exposed area of the skin, from a suitable container or applicator and, if necessary, it is then spread over and/or rubbed into the skin using the hand or fingers or a suitable device.

While the above summarizes the present invention, it will become apparent to those skilled in the art that modifications, variations and alterations may be made without deviating from the scope and spirit of the present invention as described and claimed herein. The invention will now be further illustrated in the following non-limiting examples.

EXAMPLE 1

Compositions within the scope of the invention (Composition 1-8) were compared to composition outside the scope of the invention (Compositions A-D). The compositions and observations are summarized in Tables 1 and 2.

TABLE 1

| | composition | | | | | | | |
|---|---|---|---|---|---|---|---|---|
| | 1 | 2 | 3 | 4 | 5 | 6 | 7 | 8 |
| Aminosilicone -- FORMULA 2 (Dow 8500) | 90.25 | 88.2 | 76.8 | 66.5 | 81 | | | 80 |
| Trimethylsiloxy-amodimethicone -- FORMULA 4 | | | | | | 93.1 | 80 | |
| 12HSA | 4.75 | 9.8 | 19.2 | 28.5 | 9 | 4.9 | 10 | 10 |
| Water | 5 | 2 | 4 | 5 | 10 | 2 | 10 | 10 |
| Weight Ratio aminosilicone to 12HSA | 19/1 | 9/1 | 4/1 | 2.3/1 | 9/1 | 19/1 | 7.3/1 | 7.3/1 |
| Observations | No crystals | No crystals | No crystals | No crystals | No crystals | No crystals | No crystals | No crystals |

TABLE 2

| composition | A | B | C | D |
|---|---|---|---|---|
| aminosilicone -- FORMULA 2 | 45 | 19 | 58.8 | |
| trimethylsiloxy-amodimethicone -- FORMULA 4 (Wacker ADM656) | | | | 54 |
| 12HSA | 45 | 76 | 39.2 | 36 |
| Water | 10 | 5 | 2 | 10 |

TABLE 2-continued

| composition | A | B | C | D |
|---|---|---|---|---|
| Weight Ratio aminosilicone to 12HSA | 1/1 | 0.25/1 | 1.5/1 | 1.5/1 |
| Observations | crystals | crystals | crystals | crystals |

It can be seen from the observations in Tables 1 and 2 that the weight ratio of aminosilicone to 12HSA is critical to prevent crystallization in the presence of water. The inventors have found that compositions prepared within the preferred range results in a complex formation between 12HSA and aminosilicone as evidenced by Infrared Spectroscopy. It has been found that addition of water to 12HSA-aminosilicone in the preferred range results, at low additions of water, in dispersed drops without forcing crystallization of the 12HSA.

The same examples were repeated in the absence of water. Composition 1'-4' are within the scope of the invention. Compositions A'-D' are outside the scope of the invention (ratio outside the scope). Compositions and results are summarized in Tables 1-1 and 2-1.

TABLE 1-1

| composition | 1' | 2' | 3' | 4' |
|---|---|---|---|---|
| Aminosilicone - formula 2 (Dow 8500) | 95 | 90 | 80 | 70 |
| 12HSA | 5 | 10 | 20 | 30 |
| Water | — | — | — | — |
| Weight ratio aminosilicone/12HSA | 95/5 | 90/10 | 80/20 | 70/30 |
| Observations | No crystals | No crystals | No crystals | No crystals |

TABLE 2-1

| composition | A' | B' | C' | D' |
|---|---|---|---|---|
| Aminosilicone - formula 2 (Dow 8500) | 50 | 20 | 60 | — |
| Trimethylsiloxy-amodimethicone - Formula 4 (Wacker ADM656) | — | — | — | 60 |
| 12HSA | 50 | 80 | 40 | 40 |
| Water | — | — | — | — |
| Weight ratio aminosilicone/12HSA | 1/1 | 0.25/1 | 1.5/1 | 1.5/1 |
| Observations | Crystals | Crystals | Crystals | Crystals |

It can be seen that the additive composition within the scope of the invention attain 12HSA in substantially non-crystallized form.

EXAMPLE 2

Inventive compositions (9-12) and Comparative composition (E, F) were prepared containing substantial amounts of water. Compositions and observations are summarized in Table 3.

TABLE 3

| | composition | | | | | |
|---|---|---|---|---|---|---|
| | 9 | 10 | 11 | 12 | E | F |
| Aminosilicone FORMULA 2 (Dow 8500) | 44.1 | 36 | 40.5 | 30 | 38 | 20 |
| 12HSA | 1 | 10 | 5 | 6 | 10 | 26 |
| Silica-R805 | 4.9 | 4 | 4.5 | 4 | 0 | 4 |
| water | 50 | 50 | 50 | 60 | 52 | 50 |
| Weight Ratio aminosilicone/12HSA | 49/1 | 3.5/1 | 8.1/1 | 4.9/1 | 3.8/1 | 0.77/1 |
| Observations | No crystals | No crystals | No crystals | No crystals | No crystals but water separates | Crystals |

Comparative Example E demonstrates that in the absence of particle according to the present invention, water separates out of the composition, when the water amount is relatively high. Comparative Example F demonstrates that the ration of aminosilicone to 12HSA is still critical, even in the presence of the particle.

EXAMPLE 3

Compositions outside the scope of the invention (G-L) were prepared with fatty acids other than 12HSA or silicones other than aminosilicone. Compositions and results are summarized in Table 4.

TABLE 4

| | composition | | | | | |
|---|---|---|---|---|---|---|
| | G | H | I | J | K | L |
| Aminosilicone FORMULA 2 | 88.2 | — | — | 66.5 | 76 | 40.5 |
| Dimethicone | — | 76 | — | — | — | — |

TABLE 4-continued

| | composition | | | | | |
|---|---|---|---|---|---|---|
| | G | H | I | J | K | L |
| Cyclomethicone | — | — | 72 | — | — | — |
| Stearic acid (fatty acid) | 9.8 | 19 | 18 | 28.5 | — | 5 |
| Palmitic acid (fatty acid) | — | — | — | — | 19 | — |
| Silica-R805 | — | — | — | — | — | 4.5 |
| Water | 2 | 5 | 10 | 5 | 5 | 50 |
| Weight ratio aminosilicone/fatty acid | 9/1 | - (no aminosilicone) | - (no aminosilicone) | 2.3/1 | 4/1 | 8.1/1 |
| Observations | Crystals | Crystals | Crystals | Crystals | Crystals | Crystals |

EXAMPLE 4

Compositions outside the scope of the invention (M, N) were prepared with hydrocarbon based amines instead of aminosilicones. Compositions and results are summarized in Table 5.

TABLE 5

| Composition | M | N |
|---|---|---|
| Stearamide | 85.5 | |
| n-(2(diethylamino)ethyl)stearamide | | 85.5 |
| 12HSA | 9.5 | 9.5 |
| water | 5 | 5 |
| Weight ratio aminosilicone to fatty acid | 9/1 | 9/1 |
| Observations | Crystals | Crystals |

EXAMPLE 5

A typical composition within the scope of the invention is as follows:

| Composition | |
|---|---|
| Silica - R805 | 2.88 |
| Aminosilicone Formula 2 | 2.6 |
| Silicone volatile | 23.36 |
| Water | 28.85 |
| Cyclopentasiloxane and dimethicone crosspolymer - DC9045 | 38.20 |
| Glycerine | 3.85 |
| 12HSA | 0.26 |
| Ratio aminosilicone/12HSA | 10/1 |

While described in terms of the presently preferred embodiments, it is to be understood that such disclosure is not to be interpreted as limiting. Various modifications and alterations will no doubt occur to one skilled in the art after having read the above disclosure. Accordingly, it is intended that the appended claims be interpreted as covering all such modifications and alterations as falling within the true spirit and scope of the invention.

What is claimed is:

1. A non-solid skin conditioning composition comprising:
   (a) from about 1 to about 15% by weight of the composition of 12-hydroxystearic acid, where 12-hydroxystearic acid is in substantially non-crystallized, non-solid form;
   (b) an aminosilicone wherein the weight ratio of the aminosilicone to the 12-hydroxystearic acid is from about 3:1 to about 75:1;
   (c) from about 1 to about 90% by weight of the composition of water; wherein when the water amount is greater than 20% by weight of the composition the composition further comprises a particle having an isoelectric point below the pH of the composition; wherein the composition is in the form of a leave-on and an emulsion and wherein the viscosity of the composition at 25° C. is in the range of from about 1 Pas to about 500 Pas.

2. The composition of claim 1 wherein the particle is selected from the group consisting of oxides of silicon, zinc, iron, cerium, zirconium, titanium or aluminum, stearates of zinc, magnesium, or calcium, metal silicates and mixtures thereof or the like.

3. The composition of claim 1 wherein the composition comprises at least about 20% of water and the particle comprises a silicon dioxide particle.

4. The composition of claim 1 wherein the composition is substantially free of surfactants.

5. The composition of claim 1 further comprising fumaric acid or salt thereof.

6. An additive for a skin conditioning composition comprising:
   (a) from about 1 to about 15% by weight of the composition of 12-hydroxystearic acid; and
   (b) an aminosilicone where the weight ratio of the aminosilicone to the 12-hydroxystearic acid is from about 3:1 to about 75:1.

7. A method of treating dry skin, acne, photo-damaged skin, appearance of wrinkles, age spots, aged skin, sebum overproduction, the method comprising applying to the skin the composition of claim 1.

8. A method of lightening skin color, the method comprising applying to the skin the composition of claim 1.

9. The composition of claim 1, wherein the weight ratio of the aminosilicone to the 12-hydroxystearic acid is from about 3:1 to about 49:1.

10. A skin conditioning composition comprising:
    (a) from 1 to 15% by weight of the composition of 12-hydroxystearic acid;
    (b) an aminosilicone, wherein the weight ratio of the aminosilicone to the 12-hydroxystearic acid is from 2.3:1 to 75:1;
    (c) from 1 to 90% by weight of the composition of water; wherein when the water amount is greater than 20% by weight of the composition the composition further comprises a particle having an isoelectric point below the pH of the composition; wherein the viscosity of the composition at 25° C. is in the range of from 1 Pas to 500 Pas.

11. The composition of claim 10 wherein the particle is selected from the group consisting of oxides of silicon, zinc, iron, cerium, zirconium, titanium or aluminum, stearates of zinc, magnesium, or calcium, metal silicates and mixtures thereof or the like.

12. The composition of claim 10 wherein the composition comprises at least 20% of water and the particle comprises a silicon dioxide particle.

13. The composition of claim 10, wherein the weight ratio of the aminosilicone to the 12-hydroxystearic acid is from 3:1 to 75:1.

14. The composition of claim 10, wherein the weight ratio of the aminosilicone to the 12-hydroxystearic acid is from 2.3:1 to 49:1.

15. The composition of claim 10, wherein the weight ratio of the aminosilicone to the 12-hydroxystearic acid is from 3:1 to 49:1.

* * * * *